US010226368B2

(12) United States Patent
Argentine

(10) Patent No.: US 10,226,368 B2
(45) Date of Patent: Mar. 12, 2019

(54) DELIVERY SYSTEM FOR A RETRACTABLE OUTER SHEATH

(71) Applicant: Medtronic Vascular, Inc., Santa Rosa, CA (US)

(72) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1175 days.

(21) Appl. No.: 14/259,551

(22) Filed: Apr. 23, 2014

(65) Prior Publication Data

US 2015/0305902 A1    Oct. 29, 2015

(51) Int. Cl.
*A61F 2/95* (2013.01)
*A61F 2/966* (2013.01)

(52) U.S. Cl.
CPC ...... *A61F 2/966* (2013.01); *A61F 2002/9517* (2013.01); *A61F 2002/9665* (2013.01)

(58) Field of Classification Search
CPC ...... A61F 2002/9517; A61F 2002/9665; A61F 2/2436; A61F 2/0095; A61F 2/95; A61F 2/24; A61F 2/966
USPC ...................................................... 623/1.11
See application file for complete search history.

(56) References Cited

U.S. PATENT DOCUMENTS

| 6,911,039 | B2 | 6/2005 | Shiu et al. |
| 7,105,016 | B2 | 9/2006 | Shiu et al. |
| 2005/0027305 | A1 | 2/2005 | Shiu et al. |
| 2009/0292262 | A1* | 11/2009 | Adams ............... A61F 2/2436 604/264 |
| 2011/0282425 | A1* | 11/2011 | Dwork ................ A61F 2/95 623/1.11 |
| 2012/0310332 | A1* | 12/2012 | Murray .............. A61F 2/2436 623/2.11 |

(Continued)

FOREIGN PATENT DOCUMENTS

WO    WO2011/049808    4/2011
WO    WO2012/155128    11/2012

OTHER PUBLICATIONS

PCT/US2015/026721 The International Search Report and the Written Opinion of the International Searching Authority, dated Jul. 22, 2015.

*Primary Examiner* — Jonathan Miles
*Assistant Examiner* — George J Ulsh
(74) *Attorney, Agent, or Firm* — Medler Ferro Woodhouse & Mills PLLC

(57) ABSTRACT

A delivery system for delivering a prosthesis includes a sheath, a slide shaft having a threaded outer surface, and a handle. The handle includes an internal spring assembly for selectively engaging and disengaging the handle with the threaded outer surface of the slide shaft. The internal spring assembly includes at least one spring arm, a head coupled to the spring arm and having a circumferentially rounded threaded inner surface, and a ring slidably disposed over the spring arm. When the ring is in a first longitudinal position, the threaded inner surface of the head is spaced apart from the threaded outer surface of the slide shaft. When the ring is in a second longitudinal position, the threaded inner surface of the head is threadedly engaged with the threaded outer surface of the slide shaft. The handle may include a resilient cover to provide the internal spring assembly with a biased or nominal operational position.

15 Claims, 10 Drawing Sheets

(56) References Cited

U.S. PATENT DOCUMENTS

2013/0297011 A1  11/2013  Morris et al.

* cited by examiner

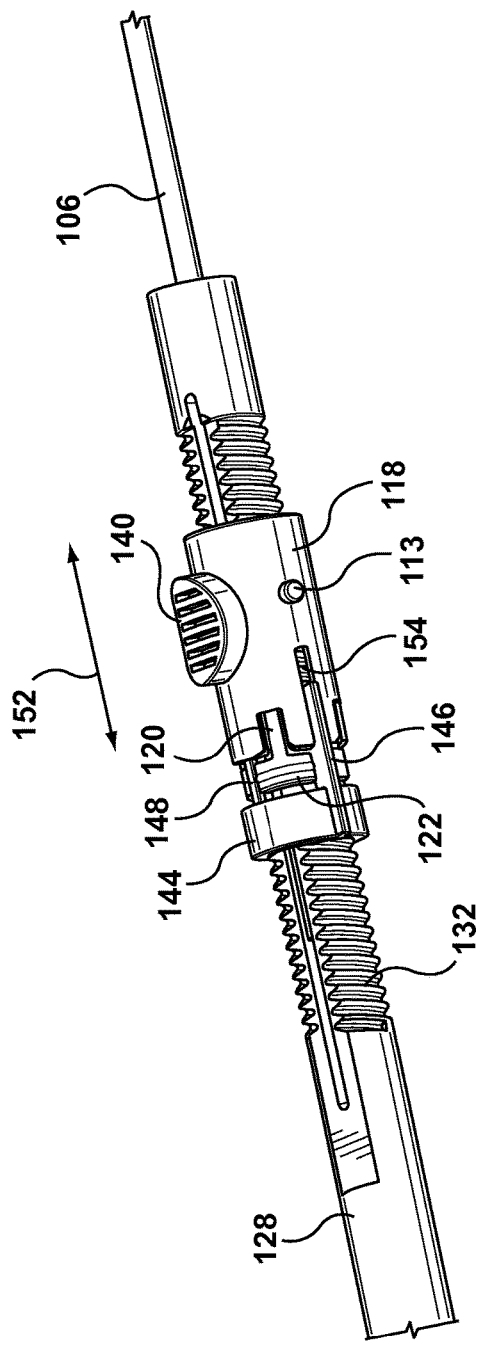
FIG. 4
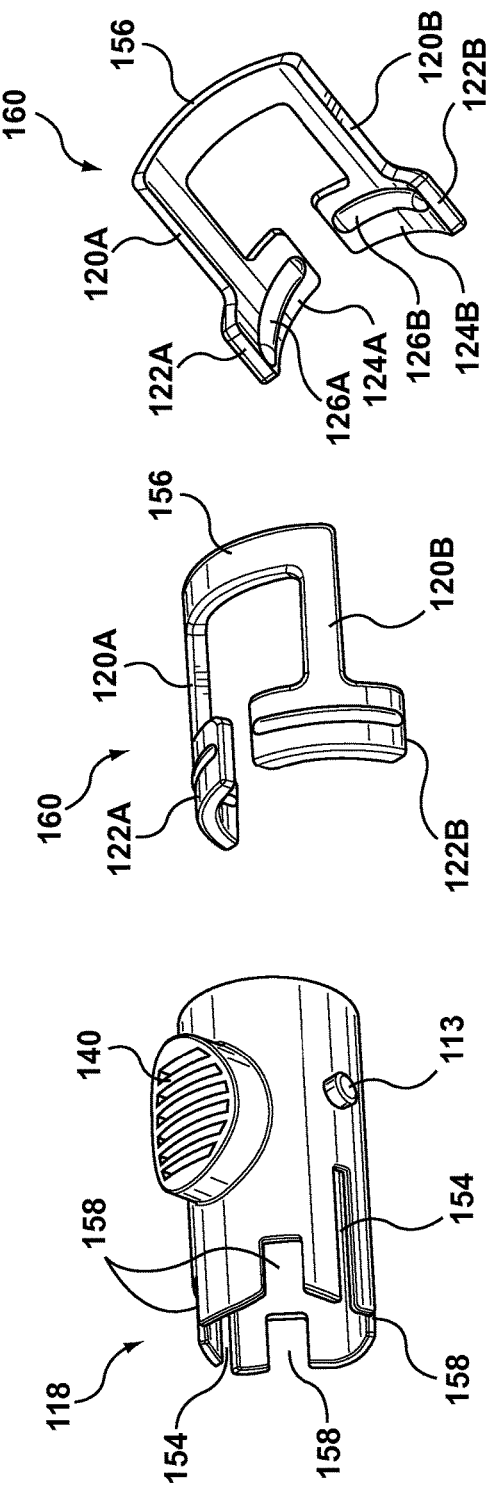
FIG. 6A
FIG. 6B
FIG. 5

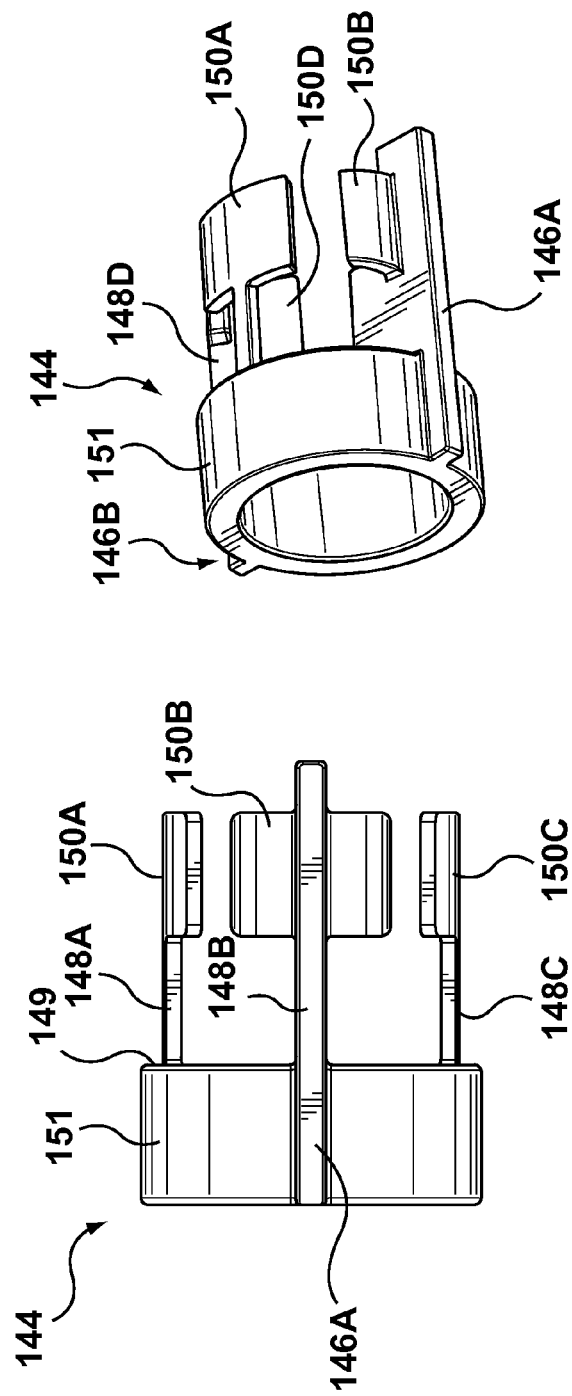
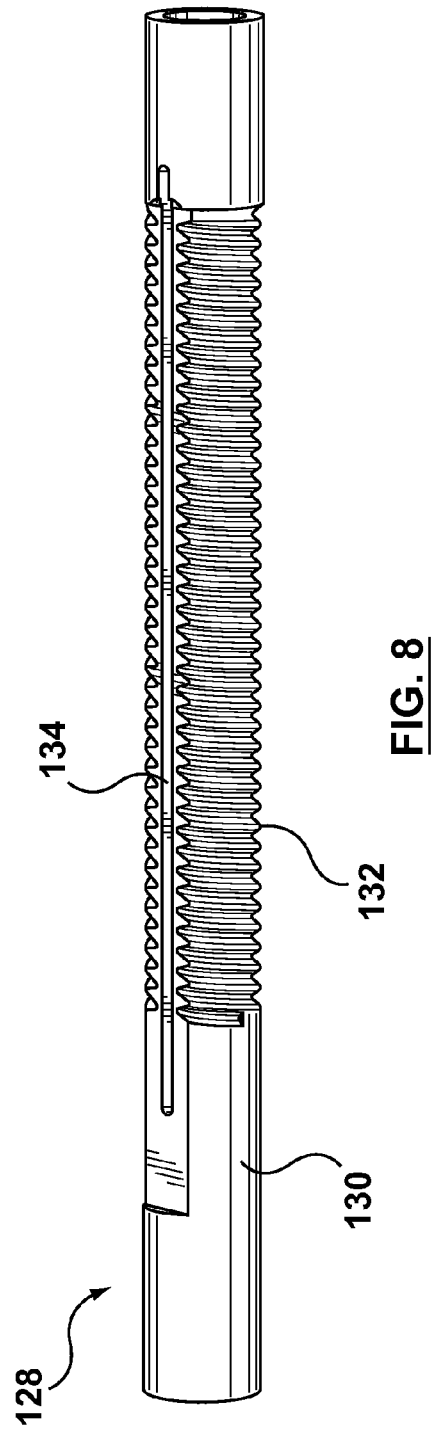
FIG. 7A
FIG. 7B
FIG. 8

DELIVERY SYSTEM FOR A RETRACTABLE OUTER SHEATH

FIELD OF THE INVENTION

Embodiments hereof relate to delivery systems and methods for deploying a prosthesis within a body lumen.

BACKGROUND OF THE INVENTION

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable biocompatible material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expandable stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes arranged for relative axial movement. For example, a self-expanding stent-graft may be compressed and disposed within the distal end of the outer tube or sheath distal of a stop fixed to the inner tube. The catheter is then maneuvered, typically routed through a body lumen until the end of the catheter and the stent-graft are positioned at the intended treatment site. The stop on the inner tube is then held stationary while the outer sheath of the delivery catheter is withdrawn. The stop prevents the stent-graft from being withdrawn with the outer sheath. As the outer sheath is withdrawn, the stent-graft is released from the confines of the outer sheath and radially self-expands so that at least a portion of it contacts and substantially conforms to a portion of the surrounding interior of the lumen, e.g., the blood vessel wall or anatomical conduit wall.

A stent-graft may be tightly compressed within a catheter for delivery, imposing high levels of friction between the stent-graft and the outer sheath of the catheter. Thus, a delivery system must be capable of imparting a significant, yet controlled, force to retract the outer sheath and deploy the stent-graft. For example, U.S. Pat. No. 6,911,039 to Shiu et al. and U.S. Pat. No. 7,105,016 to Shiu et al., both assigned to Medtronic Vascular, Inc. and each of which is herein incorporated by reference in its entirety, disclose a delivery system having a handle that utilizes a combination of axial rotation of the handle followed by axial translation, i.e., sliding, of the handle in order to retract the outer sheath of the catheter. However, a need in the art still exists for an improved delivery system having a handle that consistently and reliably retracts the outer sheath thereof in order to deploy a prosthesis in a body lumen.

Embodiments hereof relate to improvements of a delivery system having a handle configured to retract the outer sheath of the catheter.

BRIEF SUMMARY OF THE INVENTION

Embodiments hereof are related to a delivery system for delivering a prosthesis, the delivery system including a sheath, a slide shaft disposed over the sheath, and a handle coupled to a proximal end of the sheath inside of the slide shaft. The slide shaft has a threaded outer surface. The handle includes an internal spring assembly for selectively engaging and disengaging the handle with the threaded outer surface of the slide shaft. The internal spring assembly includes at least one spring arm, a head coupled to the spring arm and having a circumferentially rounded threaded inner surface, and a ring slidably disposed over the spring arm. When the ring is in a first longitudinal position, the ring is not disposed over the head and the spring arm resiliently lifts the head away from the slide shaft such that the threaded inner surface of the head is spaced apart from the threaded outer surface of the slide shaft, the handle thereby being disengaged with the threaded outer surface of the slide shaft. When the ring is in a second longitudinal position, the ring is disposed over and radially compresses at least portion of the head onto the slide shaft such that the threaded inner surface of the head is threadedly engaged with the threaded outer surface of the slide shaft, the handle thereby being engaged with the threaded outer surface of the slide shaft.

Embodiments hereof are also related to a delivery system for delivering a prosthesis, the delivery system including a sheath, a slide shaft disposed over the sheath, and a handle coupled to a proximal end of the sheath inside of the slide shaft. The slide shaft has a threaded outer surface. The handle includes an internal spring assembly for selectively engaging and disengaging the handle with the threaded outer surface of the slide shaft. The internal spring assembly includes a first spring arm, a first head coupled to the first spring arm and having a circumferentially rounded threaded inner surface, a second spring arm, a second head coupled to the second spring arm and having a circumferentially rounded threaded inner surface, a third spring arm, a third head coupled to the third spring arm and having a circumferentially rounded threaded inner surface, a fourth spring arm, a fourth head coupled to the fourth spring arm and having a circumferentially rounded threaded inner surface, and a ring slidably disposed over the first, second, third, and fourth spring arms. The circumferentially rounded threaded inner surface of each head is sized to extend over between 20% and 25% of the circumference of the threaded outer surface of the slide shaft. When the ring is in a first longitudinal position, the ring is not disposed over the first, second, third, and fourth heads and the first, second, third, and fourth spring arms resiliently lift the first, second, third, and fourth heads, respectively, away from the slide shaft such that the threaded inner surface of the first, second, third, and fourth heads are spaced apart from the threaded outer surface of the slide shaft, the handle thereby being disengaged with the threaded outer surface of the slide shaft. When the ring is in a second longitudinal position, the ring is disposed over and radially compresses at least portion of the first, second, third, and fourth heads onto the slide shaft such that the threaded inner surface of the first, second, third, and fourth heads are threadedly engaged with the threaded outer surface of the slide shaft, the handle thereby being engaged with the threaded outer surface of the slide shaft.

Embodiments hereof are also related to a delivery system for delivering a prosthesis, the delivery system including a sheath, a slide shaft disposed over the sheath, and a handle coupled to a proximal end of the sheath inside of the slide shaft. The slide shaft has a threaded outer surface. The handle includes an internal spring assembly for selectively engaging and disengaging the handle with the threaded outer surface of the slide shaft. The internal spring assembly includes at least one spring arm, a head coupled to the spring arm and having a circumferentially rounded threaded inner surface, and a ring slidably disposed over the spring arm. An actuation button is attached to and radially protruding from the ring. The handle further includes a resilient external housing disposed over the ring, the housing including an opening formed through a sidewall thereof and a groove formed within the sidewall thereof, the groove being adjacent to the opening and the actuation button extending through the opening. When the ring is in a first longitudinal position, the ring is not disposed over the head and the spring arm resiliently lifts the head away from the slide shaft such that the threaded inner surface of the head is spaced apart from the threaded outer surface of the slide shaft, the handle thereby being disengaged with the threaded outer surface of the slide shaft. When the ring is in a second longitudinal position, the ring is disposed over and radially compresses at least portion of the head onto the slide shaft such that the threaded inner surface of the head is threadedly engaged with the threaded outer surface of the slide shaft, the handle thereby being engaged with the threaded outer surface of the slide shaft. When user force is applied thereto, the groove longitudinally compresses in order to allow for sliding movement of the actuation button and when user force is not applied thereto, the groove returns to its relaxed state thereby biasing the ring in the second longitudinal position.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 4 is a perspective view of the handle of FIG. 1, wherein a housing of the handle have been removed for illustrative purposes only and the handle is in a disengaged configuration.

FIG. 5 is a perspective view of a ring of the handle of FIG. 4, wherein the ring has been removed from the handle for illustrative purposes only.

FIG. 6A is a perspective view of a spring arm subassembly of the handle of FIG. 4, wherein the spring arm subassembly has been removed from the handle for illustrative purposes only.

FIG. 6B is another perspective view of a spring arm subassembly of the handle of FIG. 4, wherein the spring arm subassembly has been removed from the handle for illustrative purposes only.

FIG. 7A is a side view of a proximal stopper of the handle of FIG. 4, wherein the proximal stopper has been removed from the handle for illustrative purposes only.

FIG. 7B is a proximal view of a proximal stopper of the handle of FIG. 4, wherein the proximal stopper has been removed from the handle for illustrative purposes only.

FIG. 8 is a perspective view of a slide shaft of the delivery system of FIG. 1, wherein the slide shaft has been removed from the delivery system for illustrative purposes only.

DETAILED DESCRIPTION OF THE INVENTION

The following detailed description is merely exemplary in nature and is not intended to limit the invention or the application and uses of the invention. Although the description of the invention is in the context of treatment of blood vessels such as but not limited to those in the abdominal and thoracic space, the invention may also be used in any other body passageways where it is deemed useful. Furthermore, there is no intention to be bound by any expressed or implied theory presented in the preceding technical field, background, brief summary or the following detailed description.

Specific embodiments of the present invention are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft prosthesis the terms "distal" and "proximal" are used herein with reference to the direction of blood flow from the heart in using the stent-graft system in the vasculature: "proximal" is the portion nearer the heart by way of blood flow path while "distal" is the portion of the stent-graft further from the heart by way of blood flow path. In addition, as used herein, axial rotation is rotation around and in a plane perpendicular to a longitudinal axis L of the handle (shown in FIG. 2). Further, axial translation or sliding is motion along longitudinal axis L.

Figure 1A:
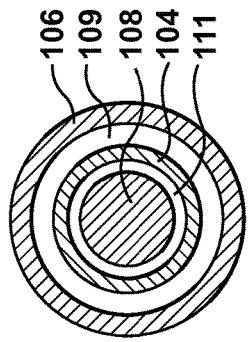
FIG. 1A is a cross-sectional view taken along line A-A of FIG. 1.
Figure 1:
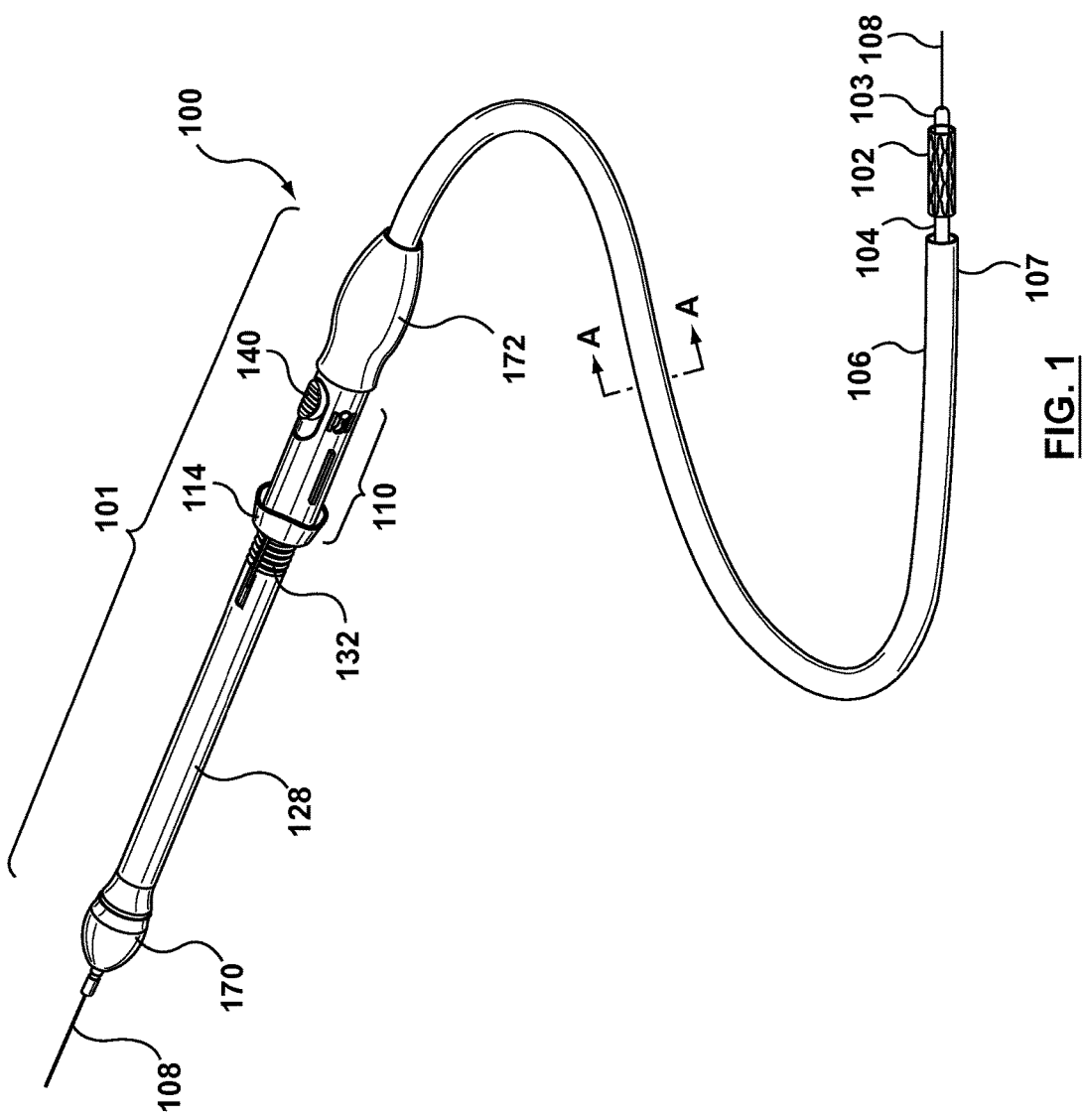
FIG. 1 is a perspective view of a delivery system having a handle for deployment of a prosthesis according to an embodiment hereof, wherein the prosthesis is in a deployed configuration.

Embodiments hereof are related to a delivery system having an improved retractor or handle for deployment of a prosthesis in a body lumen. With reference to FIGS. 1 and 1A, a delivery system 100 includes a handle assembly 101, an inner shaft 104, and an outer retractable sheath or cover 106. Handle assembly 101 includes a handle or retractor 110, a slide shaft 128, a proximal housing or stop 170 coupled to a proximal end of slide shaft 128, and a distal housing or stop 172 coupled to a distal end of slide shaft 128. Handle or retractor 110 is disposed over slide shaft 128 and may be moved between proximal stop 170 and distal stop 172. Inner shaft 104 includes a proximal end (not shown; terminates within handle assembly 101) and a distal end 103. Outer sheath 106 includes a proximal end 105 (obscured from view in FIG. 1 but shown in FIG. 3) that extends into handle 110 and a distal end 107. Outer sheath 106 defines a lumen 109 and outer sheath 106 is slidingly disposed over inner shaft 104. Inner shaft 104 defines a lumen 111 such that delivery system 100 may be slidingly disposed and track over a guidewire 108. A self-expanding prosthesis 102 is mounted over inner shaft 104 at a distal portion thereof. Prosthesis 102 is shown in its deployed or expanded configuration in FIG. 1, but it will be understood by those of ordinary skill in the art that prior to deployment, prosthesis 102 is radially compressed and restrained within distal end 107 of outer sheath 106. As will be described in more detail herein, handle 110 operates to proximally retract outer sheath 106 in order to deploy or release prosthesis 102, thereby allowing prosthesis 102 to self-expand to a deployed or expanded configuration as shown in the side view of FIG. 1. Stated another way, a user operates handle 110 of delivery system 100 in order to withdraw or proximally retract outer sheath 106, thereby releasing prosthesis 102 at a desired location in a patient's body lumen. The deployed configuration of prosthesis 102 is merely exemplary, and it would be apparent to one of ordinary skill in the art that delivery system 100 may be utilized for delivering and deploying various types or configurations of self-expanding prostheses. Further, delivery system 100 may be used for delivering any type of prosthesis that may utilize a retractable outer sheath.

Slide shaft or screw gear 128 is disposed over a proximal portion of outer sheath 106 and extends through handle 110. As will be described in more detail herein, slide shaft 128 is a tubular component that includes a thread 132 on an outer surface 130 thereof. Handle 110 includes an internal spring assembly 116 (shown in FIG. 3) for selectively engaging and disengaging the handle with the threaded outer surface 130 of slide shaft 128. When handle 110 is engaged with the threaded outer surface 130 of slide shaft 128, handle 110 must be axially rotated in order to retract outer sheath 106. Handle 110 is axially rotated around a longitudinal axis L of the handle (shown in FIG. 2). Conversely, when handle 110 is disengaged with the threaded outer surface 130 of slide shaft 128, handle 110 is slidingly disposed over slide shaft 128 and thus outer sheath 106 may be retracted by axial translation or sliding, i.e., manually pulling, handle 110. Handle 110 is axially translated or slid along longitudinal axis L of the handle.

For example, refraction of outer sheath 106 may be initiated by axial rotation of handle 110 due to high frictional forces between outer sheath 106 and prosthesis 102, and, after the frictional forces decrease, retraction of outer sheath 106 may be completed via sliding of handle 110. More particularly, it may be desirable to slowly or gradually deploy a proximal end of prosthesis 102, which is deployed first, via rotation of handle 110 when static frictional forces between prosthesis 102 and outer sheath 106 are relatively high. Gradual deployment of the proximal end of prosthesis 102 also allows an operator to verify the accuracy of the deployment position as the prosthesis initially engages the surrounding body lumen. However, since dynamic frictional forces are typically lower than static frictional forces, the frictional resistance between prosthesis 102 and outer sheath 106 decreases once outer sheath 106 begins to move. Additionally, as sheath 106 refracts, a greater length of the prosthesis is exposed by sheath 106, thereby further decreasing the frictional resistance between prosthesis 102 and outer sheath 106. Accordingly, after initial deployment of the proximal end of prosthesis 102, it may be desirable to more rapidly deploy the remaining length of prosthesis 102 via sliding of handle 110 when frictional forces between prosthesis 102 and outer sheath 106 are relatively low. Further, once the proximal end of the prosthesis has firmly engaged the surrounding body lumen, the relationship between the prosthesis and the surrounding body lumen is largely set, so that deployment can proceed safely and at a more rapid rate. By sliding handle 110 over slide shaft 128, outer sheath 106 is easily and quickly retracted thus rapidly completing deployment of prosthesis 102. Rapid deployment of prosthesis 102 facilitates faster procedure times, thus minimizing the period of time during which blood flow is occluded.

Figure 2:
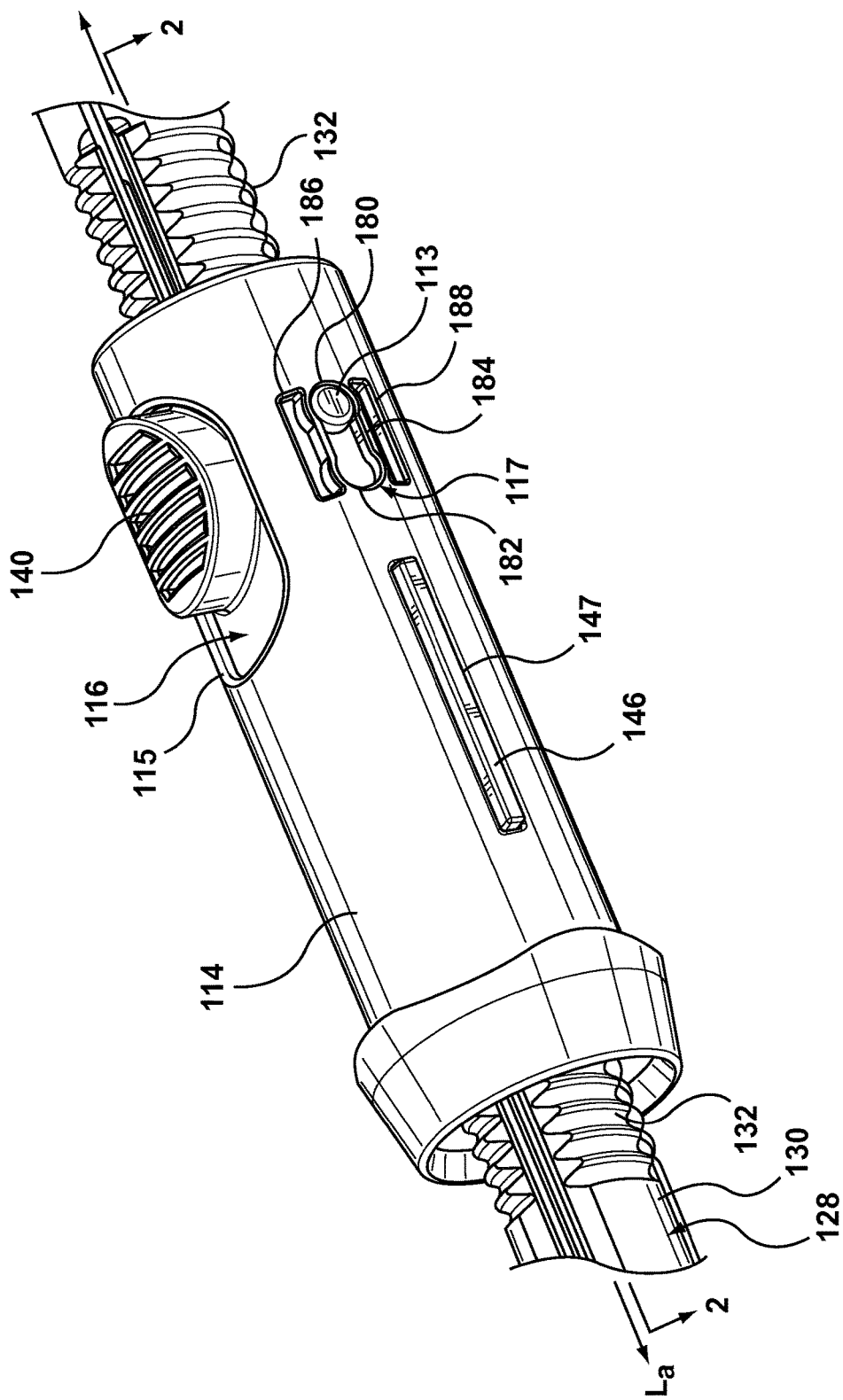
FIG. 2 is an enlarged view of the handle of FIG. 1, wherein the handle is in a disengaged configuration.
Figure 3:
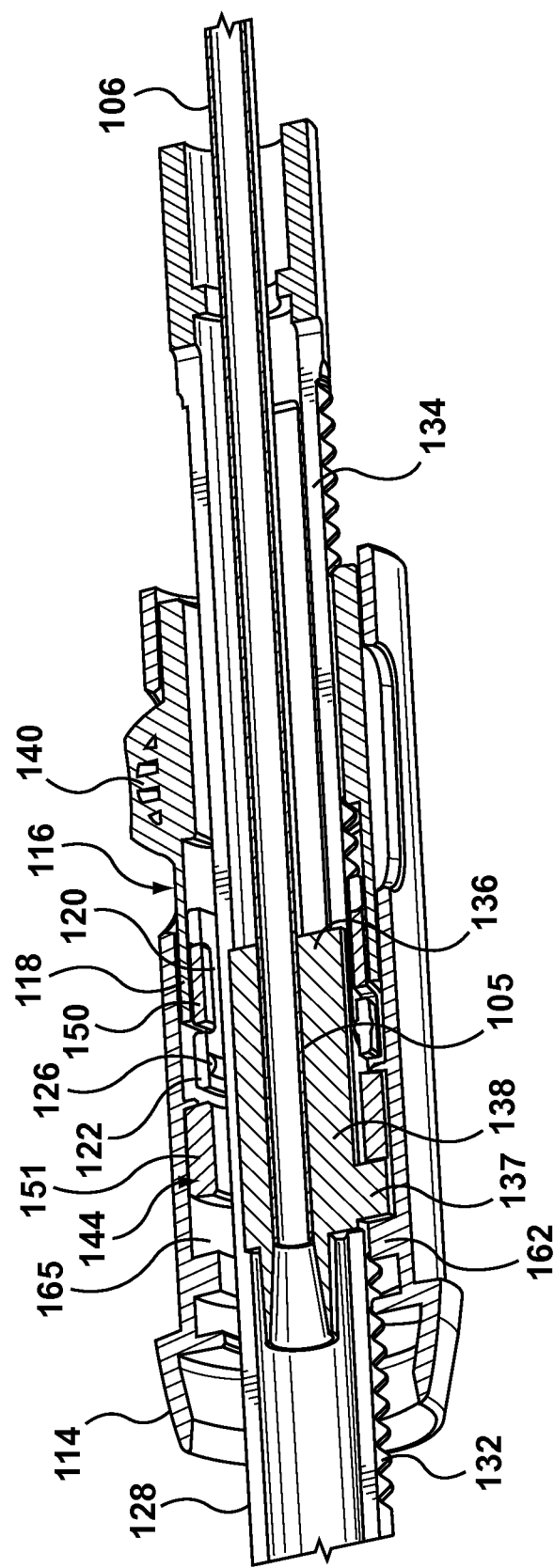
FIG. 3 is a sectional view of the handle of FIG. 1 taken along line 2-2 of FIG. 2.

Handle 110 includes a tubular housing or shell 114 which houses internal spring assembly 116. Handle 110 is best shown in FIGS. 2-4, with FIG. 2 illustrating an enlarged perspective view of handle 110 and slide shaft 128, FIG. 3 illustrating a sectional view of handle 110 and slide shaft 128 taken along line 2-2 of FIG. 2, and FIG. 4 illustrating a perspective view of handle 110 and slide shaft 128 with housing 114 of handle 110 removed for illustrative purposes only. Inner shaft 104 and guidewire 108 are not shown in the sectional view of FIG. 3 for sake of clarity.

Figure 10:
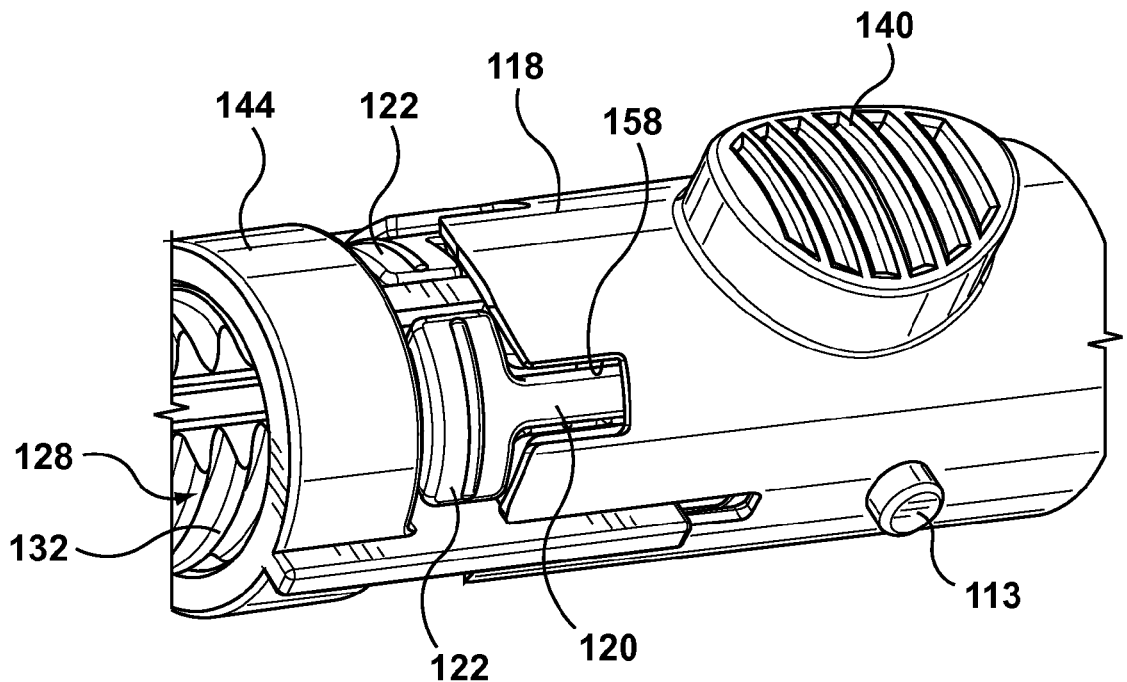
FIG. 10 is an enlarged perspective view of the handle of FIG. 4, wherein a housing of the handle have been removed for illustrative purposes only and the handle is in a disengaged configuration.
Figure 11:
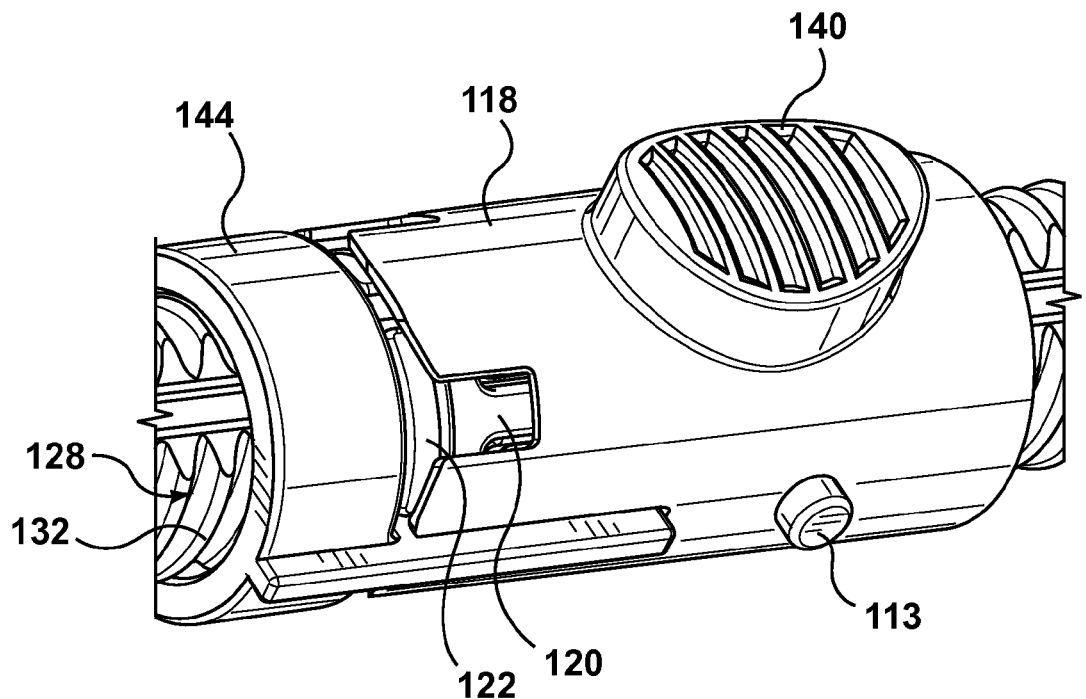
FIG. 11 is an enlarged perspective view of the handle of FIG. 4, wherein a housing of the handle have been removed for illustrative purposes only and the handle is in an engaged configuration.

Internal spring assembly 116 includes at least one spring arm 120, a head 122 coupled to spring arm 120 and having a circumferentially rounded or concave inner surface 124 with a thread 126 thereon, a ring or sleeve 118 slidably disposed over spring arm 120, and a proximal stopper 144. Ring 118 may be moved in an axial or longitudinal direction along longitudinal axis L of the handle, indicated by directional arrow 152 on FIG. 4, via an actuation button 140 which is attached to ring 118 and radially protrudes from an outer surface thereof. A knob or button 113 is also attached to ring 118 and radially protrudes from an outer surface thereof. As shown in FIGS. 2-3, actuation button 140 extends through an opening 115 of housing 114 and knob 113 extends through a shaped or contoured opening 117 of housing 114. With the exception of actuation button 140 and knob 113, internal spring assembly 116 is located within housing 114. Actuation button 140, and thus ring 118 of internal spring assembly 116 are moved by an operator relative to external housing 114 to selectively engage and disengage handle 110 from threaded outer surface 130 of slide shaft 128. As best shown in FIG. 4 and FIG. 10, when ring 118 is in a first longitudinal or axial position, ring 118 is longitudinally spaced from head 122 such that ring 118 is not disposed over head 122 of spring arm 120. Spring arm 120 resiliently lifts head 122 away from slide shaft 128 such that the threaded inner surface 124 of head 122 is spaced apart from the threaded outer surface 130 of slide shaft 128. In this position, handle 110 is disengaged with the threaded outer surface 130 of slide shaft 128. Conversely, as best shown in FIG. 11, when ring 118 is in a second longitudinal or axial position, ring 118 is disposed over and radially compresses at least a portion of head 122 onto slide shaft 128 such that the threaded inner surface 124 of head 122 is threadedly engaged with the threaded outer surface 130 of slide shaft 128. In this position, handle 110 is engaged with the threaded outer surface 130 of slide shaft 128.

In order to alternate ring 118 between the first and second longitudinal positions, the actuation button may be axially moved within opening 115 of housing 114. Advantageously, handle 110 is configured such that the user force would be required to position the handle into both configurations, i.e., the engaged configuration or the disengaged configuration, but no user force would be required to keep handle 110 in its selected position. Stated another way, once handle 110 is placed into either the engaged or disengaged configuration, the handle would remain locked in the selected configuration until an opposing user force is applied to move actuation button 140. Handle 110 is locked in the selected configuration via knob 113 of ring 118 and contoured opening 117 of housing 114, as will be explained in more detail herein with respect to FIGS. 2 and 12. Thus, the operator does not have to continuously hold actuation button 140 while retracting handle 110. Actuation button 140 only needs to be axially moved in order to selectively position handle 110 in either the engaged or disengaged configuration.

Each component of internal spring assembly 116 will be sequentially described in more detail. With reference to the perspective view of FIG. 5, ring 118 is shown removed from delivery system 100. Ring 118 is a generally tubular component that has an inner diameter slightly greater than an outer diameter of slide shaft 128 to allow ring 118 to be slipped over and disposed around slide shaft 128. As previously mentioned, ring 118 includes actuation button 140 and knob 113 attached thereto and radially extending therefrom. Ring 118, actuation button 140, and knob 113 may be integrally formed as a single component or may be separately formed components that are attached together. Ring 118 also includes two opposing longitudinal slots 154 formed through a sidewall of ring 118 at a proximal end portion of the ring. Slots 154 are sized to receive two opposing rails 146 distally extending from stopper 144, as will be described in more detail herein, and function as a guide or track for rails 146 during longitudinal movement of ring 118. In addition to slot 154, ring 118 may also include a plurality of cutout portions 158. When assembled within internal spring assembly 116, cutout portions 158 are positioned over spring arms 120 to permit spring arms 120 to resiliently lift heads 122 away from slide shaft 128. In this embodiment, as will be discussed in more detail herein, internal spring assembly 116 includes four spring arms 120 and thus include four cutout portions 158 formed on ring 118.

With reference to the perspective views of FIGS. 6A and 6B, two spring arms 120, i.e., spring arms 120A, 120B, are shown removed from delivery system 100. Heads 122A, 122B are attached to or integrally formed with spring arm 120A, 120B, respectively. Heads 122A, 122B each include a circumferentially rounded or concave inner surface 124A, 124B with threads 126A, 126B thereon. Proximal or first ends of the two spring arms 120 are attached to or integrally formed with distal ends of heads 122, and distal or second ends of the two spring arms 120 are attached to or integrally formed with a base 156 that extends between and connects the two spring arms. The assembly shown in FIGS. 6A and 6B may be considered a spring arm subassembly 160 which includes two spring arms 120 and two heads 122. In the embodiment of FIGS. 1-4, handle 110 includes two spring arm subassemblies 160 for a total of four spring arms 120 and four heads 122. Spring arms 120 and respective heads 122 are evenly positioned or spaced within housing 114 such that they are evenly positioned or spaced around the circumference of slide shaft 128.

Heads 122 are curved circumferential components that extend a portion or segment of a ring. As best shown in FIG. 6B, the inner surface 124 of each head 122 includes at least one thread or ridge 124. The threaded outer surface 130 of slide shaft 128 and the threaded inner surface 124 of heads 122 have mating rounded sinusoidal profiles (as will be described in more detail herein) such that slide shaft 128 and heads 122 may be selectively engaged to convert rotational movement into translational or linear movement. Each head is sized to extend around and contact between 20% and 25% of the circumference of slide shaft 128. As such, when four spring arms and four heads are included in the internal spring assembly as shown in the embodiment of FIG. 1-4, the four heads collectively extend over between 80% and 100% of the circumference of slide shaft 128 to maximize the mechanical advantage achieved when heads 122 are threadedly engaged with slide shaft 128. More particularly, by collectively extending over most of the circumference of slide shaft 128, the circumferentially rounded heads maximize contact with the slide shaft so that the heads cannot disengage from the slide shaft when torques and frictional resistances are the highest.

With reference to the side and perspective views of FIGS. 7A and 7B, respectively, proximal stopper 144 is shown removed from delivery system 100. Proximal stopper 144 includes a cylindrical portion 151 at a proximal end thereof and four fingers 148, i.e., fingers 148A, 148B, 148C, and 148D, extending distally from cylindrical portion 151. Four spacers 150, i.e., spacers 150A, 150B, 150C, and 150D, are attached to distal ends of fingers 148. Spacers 150 are curved circumferential components that extend around a portion or segment of a ring. Cylindrical portion 151 is a generally tubular and has an inner diameter slightly greater than an outer diameter of slide shaft 128 to allow proximal stopper 144 to be slipped over and disposed around slide shaft 128. Further, cylindrical portion 151 has a greater thickness than fingers 148 and spacers 150 such that a cylindrical abutment surface 149 is formed at a distal end of cylindrical portion 151 for contacting a proximal end of ring 118 during operation. When assembled within internal spring assembly 116, proximal stopper 144 is disposed over slide shaft 128, spring arms 120 are positioned between spacers 150, and heads 122 are positioned between fingers 148. As such, fingers 148 and spacers 150 of proximal stopper 144 mesh or intertwine with spring arms 120 and heads 122 coupled thereto to ensure correct positioning of the spring arms and heads during handle operation.

Further, as previously mentioned, proximal stopper 144 also includes two opposing rails 146, i.e., rail 146A, 146B, that radially protrude from an outer surface of proximal stopper 144. Rails 146 extend the entire length of proximal stopper 144, over the outer surfaces of cylindrical portion 151, fingers 148B, 148D, and spacers 150B, 150D. In an embodiment show in FIGS. 7A-7B, rails 146 extend slightly beyond spacers 150B, 150D. Rails 146 are sized to be slidingly received within elongated slots 154 of ring 118. In addition, as best shown in FIG. 2, rails 146 may be disposed through opposing openings 147 of housing 114, which are sized to receive rails 146. As ring 118 moves back and forth within external housing 114 during operation of handle 110, slots 154 of ring 118 slide back and forth around rails 146 of proximal stopper 114 such that the rails function as a guide or track for the slots during movement of ring 118. Although described separately, cylindrical portion 151, fingers 148, spacers 150, and rails 146 may be a single component integrally formed or one or more of the elements may be a separate component subsequently attached thereto.

When the components of internal spring assembly 116, i.e., ring 118, proximal stopper 144, and spring arms 120 having heads 122 attached thereto, are assembled, the components are coupled together via their mating structural relationships. These components are pieced together in a floating or cooperating manner and held or housed within external housing 114. More particularly, proximal stopper 144 is coupled to ring 118 via rails 146 and slots 154, respectively, as described above. Fingers 148 and spacers 150 of proximal stopper 144 are intertwined with and thereby coupled to spring arms 120 and heads 122 of spring arm subassembly 160 as described above. As such, when ring 118 is moved back and forth relative to spring arms 120 and heads 122, proximal stopper 144 prevents the inadvertent movement of spring arm subassembly 160, thereby ensuring ensure the correct positioning of the spring arms and heads for handle operation. Further, as previously mentioned, the components are held within external housing 114 because rails 146 of proximal stopper 144 extend through opposing openings 147 of housing 114 and knob 113 of ring 118 extends through contoured opening 117 of housing 114.

Turning to FIG. 8, slide shaft 128 is shown removed from delivery system 100. Slide shaft 128 is a hollow tubular member and includes at least one elongated slot 134 formed through a sidewall thereof. As described above, slide shaft 128 includes thread 132 on outer surface 130 thereof. More particularly, thread 132 is a continuous helical ridge that wraps around an outer surface of slide shaft 128. Thread 132, sometimes called a continuous thread or a series of threads, has a rounded sinusoidal profile that mates with or engages thread 126 of head 122. As used herein, a rounded sinusoidal profile of thread 132 means that the continuous helical ridge that forms thread 132 has a rounded or smooth crown and the windings of the continuous helical ridge collectively have a sinusoidal or wavelike profile. Thread 132 and thread 126 thus form a matched or mating pair of threads that are used to convert rotational to translational or linear movement as will be understood by one of ordinary skill in the art. Because ring 118 provides absolute engagement between the threaded surfaces of slide shaft 128 and heads 122, the rounded sinusoidal profile of the threads may be relatively shallow. Such a shallow thread profile advantageously results in a relatively stiff slide shaft for a smoother deployment process. In addition, since the mating threads 132, 126 are rounded rather than pointed or angular as in standard acme thread profiles, thread 126 of head 122 fully releases from thread 132 of slide shaft 128 when handle 110 is in the disengaged configuration and thus handle 110 will move or slide freely over slide shaft 128. Even if the disengaged heads 122 of spring arms 120 slightly contact slide shaft 128 during retraction of handle 110, the disengaged heads flop over the rounded or smooth crowns of thread 132. Moving or sliding freely over slide shaft 128 allows for rapid retraction of handle 110 and outer sheath 106. However, thread 132 is not required to have a rounded sinusoidal profile. In alternative embodiments, the threaded outer surface 130 of slide shaft 128 can be formed with other thread profiles which mate or engage with thread 126 of head 122.

Figure 9A:
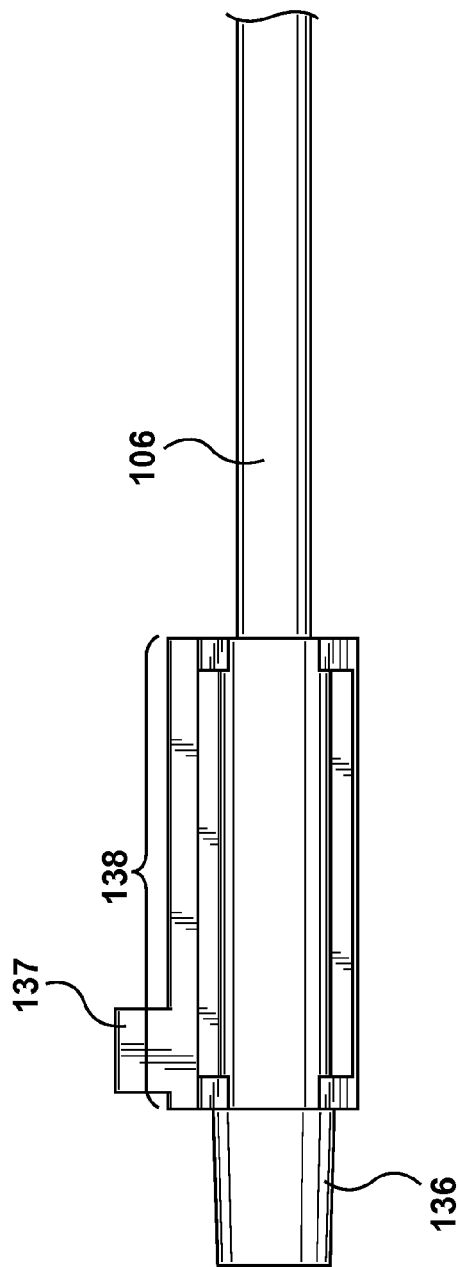
FIG. 9A is a side view of an outer sheath and coupler of the delivery system of FIG. 1, wherein the outer sheath and coupler have been removed from the delivery system for illustrative purposes only.
Figure 9B:
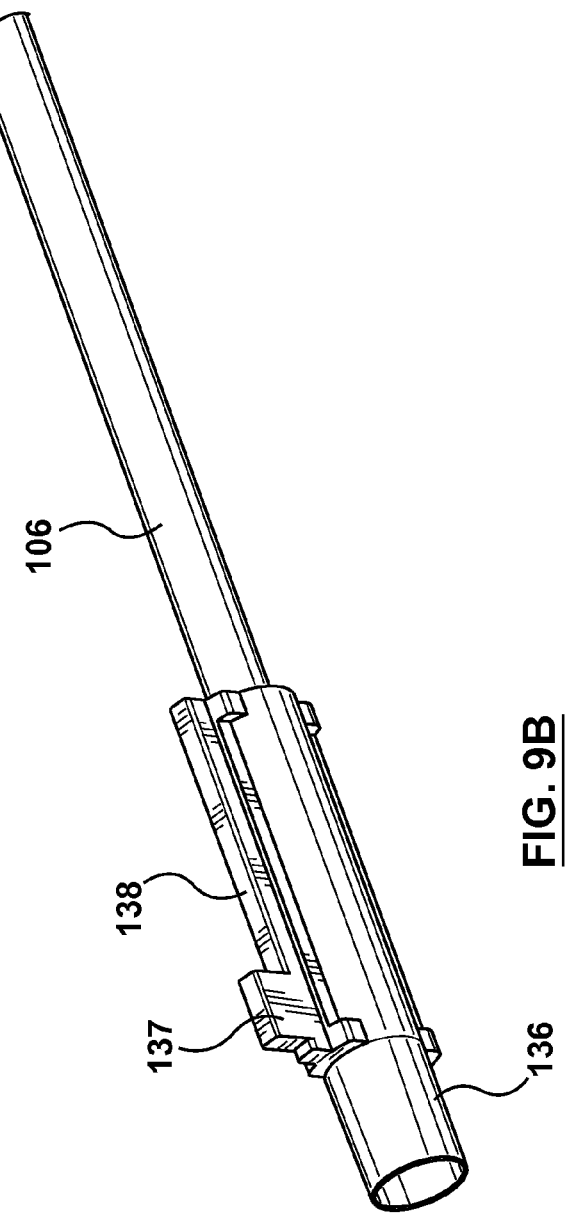
FIG. 9B is a perspective view of an outer sheath and coupler of the delivery system of FIG. 1, wherein the outer sheath and coupler have been removed from the delivery system for illustrative purposes only.

Slot 134 of slide shaft 128 allows handle 110 to be coupled to proximal end 105 of outer sheath 106. Since only a single slot is required (rather than multiple slots or openings), slide shaft 128 advantageously is relatively stiff, thereby improving the control of the relationship between the associated components for a smoother deployment process. More particularly, as shown in the side and perspective views of FIGS. 9A and 9B, respectively, a coupler 136 is attached to proximal end 105 of outer sheath 106 via overmolding, adhesive, or other mechanical method. Coupler 136 is a hollow tubular component having a rail 138 that radially protrudes therefrom. The width of rail 138 is sized to be slidingly received within slot 134 of slide shaft 128. Further, a boss or tang 137 radially protrudes from a proximal end of rail 138. When assembled within handle 110 as best shown in the sectional view of FIG. 3, tang 137 extends into a circumferential recess 165 formed between an internal ridge 162 of housing 114 and a proximal end of proximal stopper 144 to thereby couple outer sheath 106 to handle 110. With tang 137 sandwiched or wedged between internal ridge 162 of housing 114 and proximal stopper 144, force exerted upon handle 110 is transferred to outer sheath 106 such that movement of handle 110 results in movement of outer sheath 106 as will be described in more detail herein. As outer sheath 106 is retracted, slide shaft 128 is stationary and rail 138 moves within slot 134 of slide shaft 128. Although described separately, coupler 136, rail 137, and tang 138 may be a single component integrally formed or one or more of the elements may be a separate component subsequently attached thereto.

The operation of handle 110 will now be described in more detail with reference to FIGS. 10-11. FIG. 10 illustrates a perspective view of handle 110 in a first or disengaged configuration with housing 114 of handle 110 removed for illustrative purposes only. FIG. 11 illustrates a perspective view of handle 110 in a second or engaged configuration with housing 114 of handle 110 removed for illustrative purposes only. Handle 110 is selectively engaged and disengaged with threaded outer surface 130 of slide shaft 128 by sliding motion of actuation button 140, which is part of ring 118. Actuation button 140 is capable of axial translation within opening 115 of housing 114 (see sectional view of FIG. 3). Stated another way, the edges of opening 115 form proximal and distal stops for axial movement of actuation button 140 and thereby ring 118.

In the disengaged configuration of FIG. 10, heads 122 are spaced apart from or disengaged from threaded outer surface 130 of slide shaft 128 such that handle 110 is slidably mounted on or disposed over slide shaft 128. More particularly, ring 118 is in a first longitudinal or axial position such that ring 118 is not disposed over head 122 of spring arm 120 and spring arm 120, which is positioned within cutouts 158 of ring 118, resiliently lifts head 122 away from slide shaft 128 such that the threaded inner surfaces 124 of heads 122 are spaced apart from the threaded outer surface 130 of slide shaft 128. With threads 124 disengaged from thread 132 of slide shaft 128, handle 110 is slidably movable over slide shaft 128. Thus, handle 110 is easily and quickly slid over slide shaft 128. As handle 110 slides, ridge 162 or stop 144 (depending on the direction) pushes against tang 137 of coupler 136 such that coupler 136 moves with handle 110. Since coupler 136 is attached to outer sheath 106, movement of coupler 136 causes outer sheath 106 slides within slide shaft 128. Thus, when the threads of slide shaft 128 and heads 122 are not engaged, handle 110 and its internal spring assembly 116 simply slide over slide shaft 128, causing outer sheath 106 (coupled to handle 110) to slide within slide shaft 128.

With additional reference to the perspective view of FIG. 2, when ring 118 is in the first longitudinal or axial position, knob 113 of ring 118 is housed within a distal rounded end 180 of contoured opening 117. More particularly, contoured opening 117 includes a proximal rounded end 182 which is sized to receive knob 113 and distal rounded end 180 which is sized to receive knob 113. An intermediate portion or section 184 of opening 117 extends between ends 180, 182 and is sized slightly smaller than knob 113. When ring 118 is moved back and forth during operation of handle 110, knob 113 slides within contoured opening 117 between ends 180, 182. Contoured opening 117 functions as a detent and temporarily holds or locks knob 113 in either proximal rounded end 182 or distal rounded end 180. When user force is applied to move ring 118, knob 113 slides or moves through the relatively smaller intermediate section 184 of contoured opening 117. Upper and lower openings 186, 188 are located adjacent to intermediate section 184 of contoured opening 117 so that, when knob 113 is moved back and forth within intermediate section 184, the intermediate section slightly widens to allow passage of the knob. Thus, the detent provided by contoured opening 117 and knob 113 configures handle 110 to remain locked in the selected configuration (i.e., the engaged configuration or the disengaged configuration) until an opposing user force is applied to move ring 118.

Figure 12:
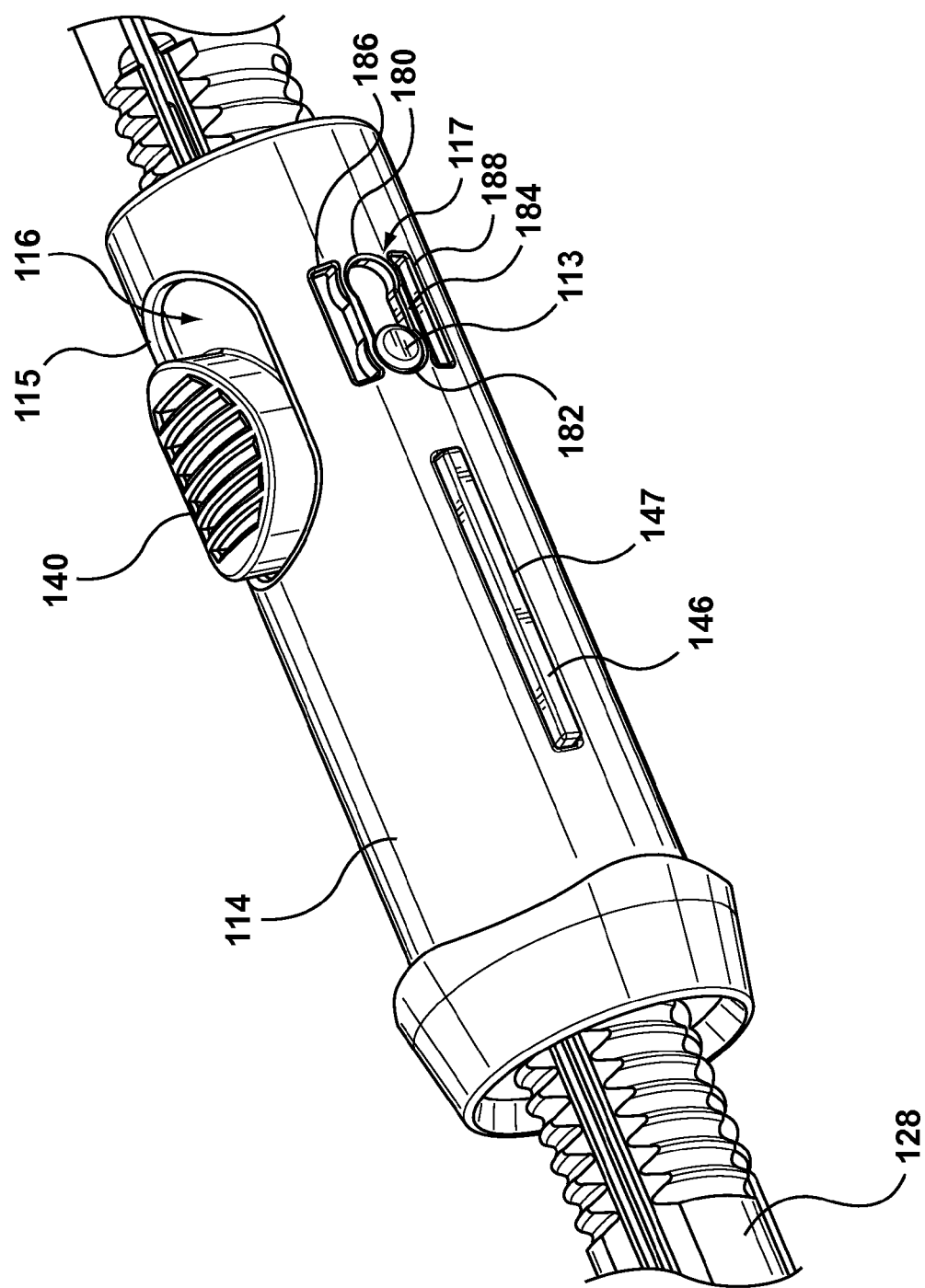
FIG. 12 is an enlarged view of the handle of FIG. 1, wherein the handle is in an engaged configuration.

FIGS. 11 and 12 illustrate the engaged configuration of handle 110. In the engaged configuration, heads 122 are forced to engage threaded outer surface 130 of slide shaft 128 such that handle 110 is rotatably mounted on or disposed over slide shaft 128. More particularly, as best shown in FIG. 11, ring 118 has been proximally retracted to a second longitudinal or axial position such that ring 118 is disposed over and radially compresses at least portion of head 122 onto slide shaft 128 such that the threaded inner surface 124 of head 122 is threadedly engaged with the threaded outer surface 130 of slide shaft 128. When threads 126, 132 of heads 122, slide shaft 128, respectively, are engaged, handle 110 must be rotated relative to slide shaft 128 in order to retract outer sheath 106. As will be explained in more detail herein, the engagement of threaded inner surface 124 of head 122 and threaded outer surface 130 of slide shaft 128 converts axial rotation of handle 110 into axial translation, i.e., retraction, of outer sheath 106. When handle 110 is in the engaged configuration, release forces are improved due to the mechanical advantage of the threaded relationship. The rotational forces to rotate the handle and thereby retract the outer sheath are significantly less than forces required to slide or proximally retract the handle and outer sheath coupled thereto. The mechanical advantage of the threaded relationship helps the physician to overcome the relatively larger static frictional resistance between prosthesis 102 and outer sheath 106, and may also help overcome any invagination of prosthesis 102 into outer sheath 106.

Handle 110 is coupled to outer sheath 106 such that rotation of handle 110 causes retraction of outer sheath 106 when handle 110 is in the engaged configuration. More particularly, during rotation of handle 110, slide shaft 128 is held stationary. Since coupler 136 extends through stationary slide shaft 128 via slot 134, outer sheath 106 and coupler 136 do not rotate (or are prevented from rotating with) with handle 110. The circumferential recess formed between internal ridge 162 of housing 114 and proximal stopper 144 houses tang 137 of coupler 136 during rotation of handle 110, essentially permitting handle 110 to spin or rotate around coupler 136 since outer sheath 106 and coupler 136 are prevented from rotating with handle 110. With outer sheath 106 being prevented from rotating, rotation of handle 110 and its internal spring assembly 116 results in relative rotation between handle 110 and slide shaft 128 along threads 126, 134. When threads 126, 132 of heads 122, slide shaft 128, respectively, are engaged, rotation of handle 110 is converted to axial translation of handle 110. When handle 110 is axially translated, ridge 162 of housing 114 or cylindrical portion 151 of proximal stopper 144 (depending upon the rotational direction of handle 110) pushes against tang 137 of coupler 136, thereby pushing or causing coupler 136 to move. Since coupler 136 is attached to proximal end 105 of sheath 106, sheath 106 moves with coupler 136. Thus, due to the threaded relationship there-between, the rotational movement of handle 110 is converted to or causes translational or linear movement of outer sheath 106 coupled thereto such that the outer sheath is longitudinally driven back or forth along the main or longitudinal axis $L_A$ of the handle to release and deploy the prosthesis. If handle 110 is rotated in a first direction, i.e. clockwise or counter-clockwise depending upon the direction of the threaded connection 126, 134 between handle 110 and slide shaft 128, outer sheath 106 may be proximally retracted to release or deploy prosthesis 102.

As best shown in FIG. 12, when ring 118 is in the second longitudinal or axial position, knob 113 of ring 118 is housed within proximal rounded end 182 of contoured opening 117. As described above, the detent provided by contoured opening 117 and knob 113 configures handle 110 to remain locked in the selected configuration (i.e., the engaged configuration or the disengaged configuration) until an opposing user force is applied to move ring 118.

As previously described herein, it may be desirable to position handle 110 in the engaged configuration of FIG. 11 during initial retraction of outer sheath 106 when deploying the proximal end of prosthesis 102. After the proximal end of prosthesis 102 is deployed via axial rotation of handle 110, it may be desirable to position handle 110 in the disengaged configuration of FIG. 10 in order to rapidly complete deployment of the prosthesis. The handle 110 may be positioned in the engaged configuration during any period of the deployment process in which the physician desires more mechanical advantage and/or control of sheath 106. Further, although sheath 106 is described above as being refracted by the combination of axial rotation of handle 110 followed by axial translation of handle 110, sheath 106 may be retracted entirely by axial rotation of handle 110 or entirely by axial translation of handle 110.

Further, as described herein, handle 110 is positioned into the engaged configuration of FIG. 11 via proximal retraction of ring 118 relative to spring arm 120 and handle 110 is positioned into the disengaged configuration of FIG. 10 via distal advancement of ring 118 relative to spring arm 120. Ring 118 may be selectively moved between the engaged and disengaged configuration via sliding motion of actuation button 140 within opening 115 of housing 114. In this embodiment, opening 115 (and actuation button 140) is positioned near the distal end of housing 114 and stopper 114 is positioned within housing 114 near the proximal end thereof. However, it should be noted that this configuration is exemplary and is not meant to be limiting. As will be understood by one of ordinary skill in the art, internal spring assembly 116 may be disposed within housing 115 in a variety of configurations. For example, opening 115 (and actuation button 140) may alternatively be positioned near the proximal end of housing 114 and the stopper may be positioned within the housing near the distal end thereof. In such a configuration, the handle would be positioned in the engaged configuration via distal advancement of the ring relative to the spring arm and the handle would be positioned in the disengaged configuration via proximal retraction of the ring relative to the spring arm.

Figure 13:
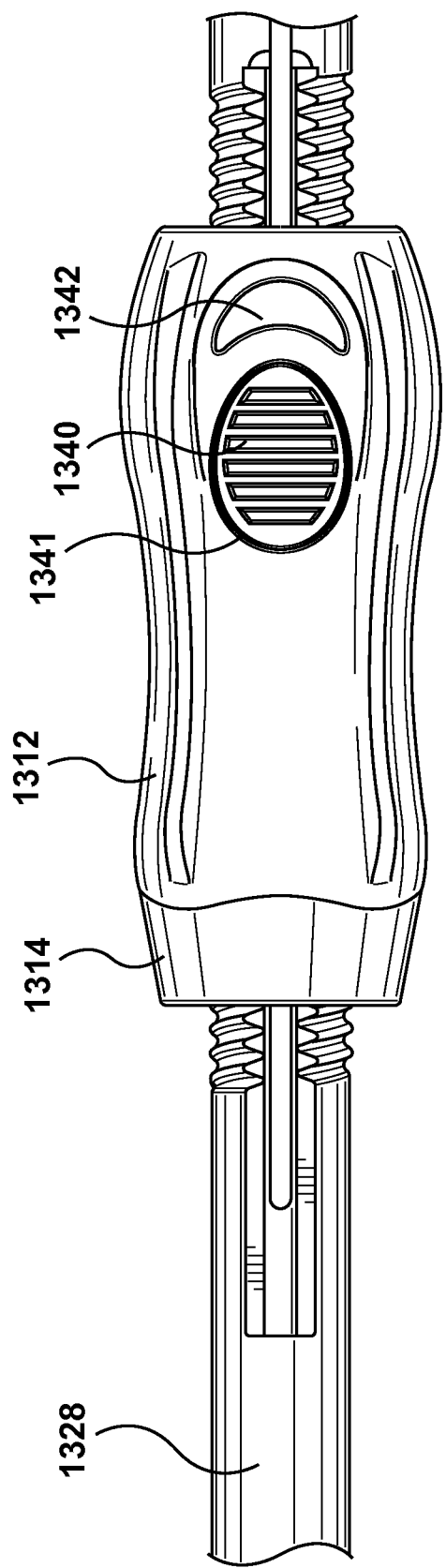
FIG. 13 is an enlarged view of a handle according to another embodiment hereof, wherein the handle includes a resilient cover for biasing the handle in the engaged configuration.

As previously described, once handle 110 is placed into either the engaged or disengaged configuration, the handle would remain locked in the selected configuration until an opposing user force is applied to move the actuation button. However, in another embodiment hereof, the detent provided by contoured opening 117 and knob 113 may be omitted and the internal spring assembly may be configured with a biased or nominal operational position, i.e., the handle may be biased to be engaged with the slide shaft. In such an embodiment, the handle returns to its biased or nominal operational configuration when no user force is applied thereto. More particularly, as shown in FIG. 13, handle 1310 includes a resilient cover or boot 1312 disposed over and surrounding an external housing 1314. Resilient cover 1312 operates to bias the internal spring assembly in the engaged configuration in which the handle is engaged with the slide shaft. User force is thus required to position and keep the internal spring assembly in the disengaged configuration in which the handle is engaged with the slide shaft. Without application of user force, or when user force is removed, cover 1312 resiliently pushes an actuation button 1340 and the remaining components of internal spring assembly (not shown in FIG. 13) into the engaged configuration. Stated another way, resilient cover 1312 is a spring-loaded mechanism that in its relaxed or nominal state biases the handle into the engaged configuration.

Figure 14:
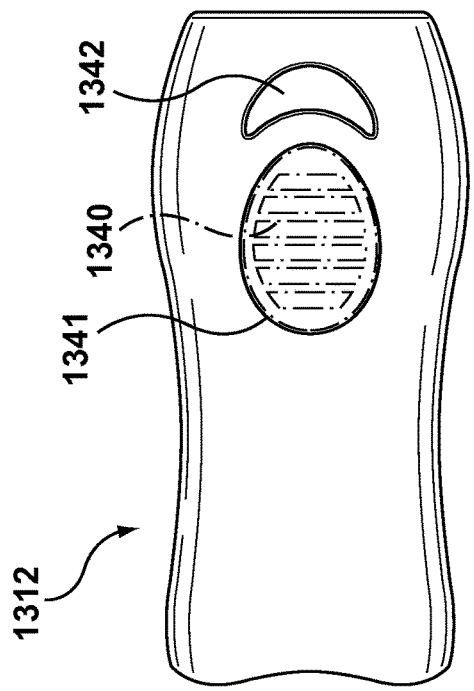
FIG. 14 is a perspective view of the resilient cover of FIG. 13, wherein the resilient cover has been removed from the handle for illustrative purposes only and is in its relaxed or nominal state.

More particularly, with additional reference to FIG. 14, resilient cover 1312 is shown removed from a delivery system and is shown in its relaxed or nominal state. Resilient cover 1312 is a tubular component that surrounds external housing 1314 and includes opening 1341 formed through a sidewall thereof. Resilient cover 1312 is formed from a resilient material such as but not limited to silicone. Opening 1341 is sized only slightly larger than actuation button 1340, which is showed in phantom in FIGS. 14 and 15. Actuation button 1340 extends through an opening (obscured from view in FIG. 13) of external housing 1314, as well as opening 1341 in resilient cover 1312. The openings of housing 1314 and resilient cover 1312 are aligned, although the opening in external housing 1314 is longer than opening 1341 as described in more detail herein.

A groove 1342 is formed within a sidewall of resilient cover 1312, distal to a distal end of opening 1341. In this embodiment, groove 1342 is a crescent shaped in order to match the profile of the distal end of opening 1341 which is oval shaped. However, the shapes or both opening 1341 and groove 1342 are exemplary and not intended to be limiting. Collectively, groove 1342 and opening 1341 extend the length of the opening of housing 1314.

Figure 15:
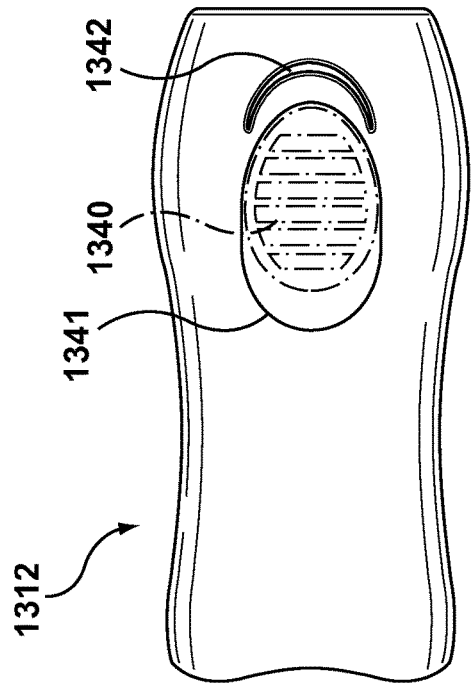
FIG. 15 is a perspective view of the resilient cover of FIG. 14, wherein the resilient cover is in its deformed or compressed state.

When resilient cover 1312 is in its relaxed or nominal state, actuation button 1340 extends through opening 1341 thereof and groove 1342 is not deformed in any manner as shown in FIG. 14. Although not shown, in this embodiment the internal spring assembly is positioned in the engaged configuration in which the ring extends over and compresses the heads of the spring arms. When it is desired to position the handle into the disengaged configuration, actuation button 1340 is distally advanced (via application of user force) and thereby longitudinally compresses or deforms groove 1342 as shown in FIG. 15. Groove 1342, having a reduced thickness compared to the rest of resilient cover 1312, permits sliding movement or distal advancement of actuation button 1340 (i.e., the reduced material thickness makes it easier for the operator to deform resilient cover 1312 and distally advance actuation button 1340). Distal advancement of actuation button 1340 results in distal advancement of the ring such that the ring does not extend over the heads of the spring arms. When the user force is removed, the resilient material of cover 1312 causes groove 1342 to spring back to its relaxed or nominal state of FIG. 14, thereby proximally retracting or pushing actuation button 1340 and the ring coupled thereto such that the handle reverts back into the engaged configuration. Thus, in this embodiment, user force is required to position and keep the handle in the disengaged configuration. An operator must therefore press or hold actuation button 1340 to keep the handle in the disengaged configuration and axially slide or translate the handle over the slide shaft.

As previously stated, as will be understood by one of ordinary skill in the art, the internal spring assembly of embodiments hereof may be disposed within the external housing in a variety of configurations. In the embodiment of FIGS. 13-15, opening 1315 (and actuation button 1340) is positioned near the distal end of housing 1314 and the proximal stopper (not shown in FIGS. 13-15) of the internal spring assembly is positioned within housing 1314 near the proximal end thereof. As such, handle 1310 has a default or nominal engaged configuration and actuation button 1340 is distally advanced, thereby longitudinally compressing or deforming groove 1342 as shown in FIG. 15, in order to position handle 1310 into the disengaged configuration. However, it should be noted that this configuration is exemplary and is not meant to be limiting. For example, if it is determined that it is more desirable for a user to proximally retract the actuation button in order to position the handle into the disengaged configuration, the components of the internal spring assembly may be re-positioned such that the actuation button is proximally retracted, thereby longitudinally compressing or deforming a groove which is positioned proximal to the actuation button, in order to position the handle into the disengaged configuration.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery system comprising:
   a sheath;
   a slide shaft disposed over the sheath, wherein the slide shaft has an outer surface including a slide shaft thread; and
   a handle coupled to a proximal end of the sheath inside of the slide shaft, the handle including an internal spring assembly for selectively engaging and disengaging the handle with the threaded outer surface of the slide shaft, the internal spring assembly including a first spring arm and a first head coupled to the first spring arm, a second spring arm and a second head coupled to the second spring arm, a third spring arm and a third head coupled to the third spring arm, and a fourth spring arm and a fourth head coupled to the fourth spring arm, each of the first head, second head, third head, and fourth head having a circumferentially rounded inner surface, each of the inner surfaces including a head thread, and a ring slidably disposed over the first, second, third and fourth spring arms, the circumferentially rounded threaded inner surface of each head is sized to extend over between 20% and 25% of the circumference of the threaded outer surface of the slide shaft,
   wherein when the ring is in a first longitudinal position, the ring is not disposed over the head and the spring arm resiliently lifts the head away from the slide shaft such that the threaded inner surface of the head is spaced apart from the threaded outer surface of the slide shaft, the handle thereby being disengaged with the threaded outer surface of the slide shaft,
   wherein when the ring is in a second longitudinal position, the ring is disposed over and radially compresses at least a portion of the head onto the slide shaft such that the threaded inner surface of the head is threadedly engaged with the threaded outer surface of the slide shaft, the handle thereby being engaged with the threaded outer surface of the slide shaft,
   wherein the slide shaft thread has a rounded sinusoidal profile and the head thread has a rounded profile that mates with the slide shaft thread in the second longitudinal position of the ring.

2. The delivery system of claim 1, wherein axial rotation of the handle proximally retracts the sheath when the handle is engaged with the threaded outer surface of the slide shaft and wherein axial translation of the handle proximally retracts the sheath when the handle is disengaged with the threaded outer surface of the slide shaft.

3. The delivery system of claim 1, wherein the first spring arm is coupled to a proximal end of the first head and the second spring arm is coupled to a proximal end of the second head, and a base extends between and connects proximal ends of the first and second spring arms.

4. The delivery system of claim 1, wherein the threaded outer surface of the slide shaft and the threaded inner surface of the first, second, third, and fourth heads have matching circumferential profiles.

5. The delivery system of claim 1, wherein an actuation button is attached to the ring and radially protrudes from an outer surface thereof.

6. The delivery system of claim 5, wherein the handle also includes an external housing and a cover formed of a resilient material surrounding the external housing, the actuation button extending through openings formed through the external housing and cover, wherein a groove is formed within the cover and the groove allows for sliding movement of the actuation button with user force applied thereto and biases the ring in the second longitudinal position without user force applied thereto.

7. The delivery system of claim 6, wherein the handle also includes an external housing having a contoured opening and a knob is attached to the ring and radially protrudes from the outer surface thereof, the knob extending through the contoured opening of the external housing, wherein the contoured opening and knob form a detent that locks the ring into the first and second longitudinal positions without user force applied thereto.

8. The delivery system of claim 7, wherein the contoured opening includes a proximal rounded end sized to receive the knob, a distal rounded end sized to receive the knob, and an intermediate section extending between the proximal and distal rounded ends, the intermediate section being sized smaller than the knob.

9. The delivery system of claim 1, wherein the slide shaft includes one slot and a tubular coupler is attached to the proximal end of the sheath, the coupler having a rail radially protruding therefrom that extends through the slot of the slide shaft to couple the sheath to the handle.

10. The delivery system of claim 1, wherein the internal spring assembly further includes a stopper that ensures correct positioning of the spring arm and head relative to the ring.

11. The delivery system of claim 1, further comprising a prosthesis within a distal end of the sheath.

12. A delivery system comprising:
    a sheath;
    a slide shaft disposed over the sheath, wherein the slide shaft has a threaded outer surface; and
    a handle coupled to a proximal end of the sheath inside of the slide shaft, the handle including an internal spring assembly for selectively engaging and disengaging the handle with the threaded outer surface of the slide shaft, the internal spring assembly including a spring arm, a head coupled to the spring arm and having a circumferentially rounded threaded inner surface, and a ring slidably disposed over the spring arm, an actuation button being attached to and radially protruding from the ring,
    wherein the handle further includes a resilient tubular cover disposed over the ring, the cover including an opening formed through a sidewall thereof and a groove formed within the sidewall thereof, the groove being adjacent to the opening and the actuation button extending through the opening,
    wherein when the ring is in a first longitudinal position, the ring is not disposed over the head and the spring arm resiliently lifts the head away from the slide shaft such that the threaded inner surface of the head is spaced apart from the threaded outer surface of the slide shaft, the handle thereby being disengaged with the threaded outer surface of the slide shaft,
    wherein when the ring is in a second longitudinal position, the ring is disposed over and radially compresses at least portion of the head onto the slide shaft such that the threaded inner surface of the head is threadedly engaged with the threaded outer surface of the slide shaft, the handle thereby being engaged with the threaded outer surface of the slide shaft, and wherein when user force is applied to the actuation button in a longitudinal direction toward the groove, the groove longitudinally compresses in order to allow for sliding movement of the actuation button and when user force is not applied to the actuation button, the groove returns to a relaxed state thereby biasing the ring in the second longitudinal position.

13. The delivery system of claim 12, wherein the groove has a crescent configuration.

14. The delivery system of claim 12, wherein the cover is formed from silicone.

15. The delivery system of claim 12, wherein axial rotation of the handle proximally retracts the sheath when the handle is engaged with the threaded outer surface of the slide shaft and wherein axial translation of the handle proximally retracts the sheath when the handle is disengaged with the threaded outer surface of the slide shaft.

\* \* \* \* \*